US00PP13925P39

(12) United States Plant Patent
Zary

(10) Patent No.: US PP13,925 P3
(45) Date of Patent: Jul. 1, 2003

(54) HYBRID TEA ROSE PLANT NAMED 'JACWORRO'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/000,385

(22) Filed: Nov. 30, 2001

(65) Prior Publication Data

US 2003/0106114 P1 Jun. 5, 2003

(51) Int. Cl.[7] ..... A01H 5/00

(52) U.S. Cl. ..... Plt./134

(58) Field of Search ..... Plt./134, 104

*Primary Examiner*—Howard J. Locker
(74) *Attorney, Agent, or Firm*—Klarquist Sparkman, LLP

(57) ABSTRACT

Hybrid tea rose plant having a light yellow flower color, good flower form, anise fragrance, long cut flower vase life, vigorous upright growth habit and large bloom size.

1 Drawing Sheet

SUMMARY OF THE INVENTION

The present invention relates to a new and distinct variety of rose plant of the hybrid tea class which was originated by me by crossing the variety JACyap (unpatented) with an unnamed seedling (unpatented).

BACKGROUND OF THE INVENTION

The primary objective of this breeding was to produce a new rose variety having the vigorous upright habit and good hybrid tea flower form of the yellow and pink flowered female parent combined with the bright yellow flower color and good flower form of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Light yellow flower color;
2. Good flower form;
3. Anise fragrance;
4. Long cut flower vase life;
5. Vigorous upright growth habit; and
6. Large bloom size.

Asexual reproduction of this new variety by budding, as performed at Wasco, Calif., shows that the foregoing and all other characteristics and distinctions come true to form and are established and transmitted through succeeding propagations.

COMPARISION WITH PARENTS

'JACworro' differs from the female parent in having pure light yellow flowers and an anise scent. 'JACworro' differs from the male parent in having lighter yellow flowers and a more vigorous upright plant.

COMPARISON WITH SIMILAR VARIETY

The flower color is an unusual pure light yellow coupled with a pleasant anise fragrance. Combined with its good flower form, JACworro is unlike any other yellow garden rose of which I am aware.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) colour chart, except where ordinary dictionary significance of color is indicated.

Parentage:
*Seed parent.*—JACyap.
*Pollen parent.*—Unnamed seedling. (Unnamed seedling×Sun Glory).
Classification:
*Botanical.*—*Rosa hybrida.*
*Commercial.*—Hybrid tea.

FLOWER

Observations made from plants of two years of age grown in a garden environment at Somis, Calif. in January, 2000 to August 2001.

Blooming habit: Continuous.
Bud:
*Size.*—About 28–30 mm long when the petals start to unfurl.
*Form.*—The bud form is pointed ovoid.

*Color.*—When sepals first divide, bud color is Yellow Group 12A. When half blown, the upper sides of the petals are Yellow Group 12A with Yellow Group 8B on the tip; and the lower sides of the petals are Yellow Group 12A with Yellow Group 10B on the tip.

*Sepals.*—Color: Yellow-Green Group 144A with Yellow-Green Group 144B on the base and Greyed-Purple 183B on the tips of the appendaged sepals. Length: 38–42 mm. Width: 9–11 mm. Shape: Subulate. Surface texture: Upper: Hoary; Lower: Smooth. There are three normally appendaged sepals. There are two unappendaged sepals with hairy edges.

*Receptacle.*—Color: Yellow-Green Group 145A. Shape: Pear. Size: Medium, about 8 mm long×10 mm wide. Surface: Smooth.

*Peduncle.*—Length: Short, averaging about 55–80 mm. Surface: Glandular. Color: Yellow-Green Group 144A. Strength: Erect, some bend a little due to large blooms.

Bloom:

*Size.*—Large. Average open size is 9–11 cm.

*Borne.*—Singly.

*Stems.*—Strength: Normal. Average length is about 30–40 cm.

*Form.*—When first open: High centered. Permanence: Outer petal edges curl slightly.

*Petalage.*—Number of petals under normal conditions: 40–45.

*Color.*—The upper sides of the petals are Yellow Group 8B with Yellow Group 9B at the base. The reverse sides of the petals are Yellow Group 8C with Yellow Group 9B at the base. The major color on the upper side is Yellow Group 8B.

*Variegations.*—None.

*Discoloration.*—The general tonality at the end of the first day: Yellow Group 8B. At the end of the third day: Yellow Group 8B.

*Fragrance.*—Moderate, anise.

Petals:

*Texture.*—Thick.

*Shape.*—Round.

*Margin.*—Smooth.

*Apex shape.*—Retuse.

*Base shape.*—Rounded.

*Form.*—Tips slightly recurved.

*Arrangement.*—Imbricated. No petaloids.

*Persistence.*—Petals hang on and dry.

*Lastingness.*—On the plant: Long (about 8–10 days). As a cut flower: Long (about 9–11 days).

Reproductive parts:

*Stamens.*—Number: 210–230. Length: 12–15 mm. Arrangement: Regular around styles. Anthers: Size: 3–4 mm. Length: 12–15 mm. Color: Yellow-Orange Group 21B. Arrangement: Regular around styles. Filaments: Color: Outer surface: Yellow Group 3C. Inner surface: Red Group 39A. Length: 9–11 mm. Pollen: Color: Yellow-Orange Group 17C.

*Pistils.*—Number: 180–200. Styles: Color: Yellow-Orange Group 20D. Length: 6–8 mm. Stigmas: Color: Yellow Group 12C. Length: 1 mm.

*Hips.*—None observed.

Plant:

*Form.*—Bush.

*Growth.*—Vigorous, upright and branching.

*Mature plant.*—Height: 1.5 m. Width: 1.2 m.

*Rootstock.*—Dr. Huey.

Foliage: Number of leaflets on normal mid-stem leaves: 5–7.

*Size.*—Medium. (14–18 cm long×9–11 cm wide).

*Quantity.*—Normal.

*Color.*—New foliage: Upper side: Greyed-Purple Group 183B. Lower side: Greyed-Purple Group 183D. Old foliage: Upper side: Yellow-Green Group 147A. Lower side: Yellow-Green Group 147C.

Leaflets:

*Size.*—Length: 5–6 cm. Width: 3–4 cm.

*Shape.*—Ovate.

*Base shape.*—Rounded.

*Apex shape.*—Mucronate.

*Texture.*—Glossy.

*Edge.*—Serrated.

*Serrations.*—Single, small.

*Petiole color.*—Yellow-Green Group 145B.

*Petiole rachis.*—Color: Upper surface: Green Group 137C with Yellow-Green Group 145B on midrib; Lower surface: Yellow-Green Group 144C with prickles.

*Auricle shape, if present.*—Subulate.

*Stipules.*—Medium, bearded (Length about 18–24 mm.)

*Disease resistance.*—Susceptible to mildew, resistant to blackspot and rust under normal growing conditions.

*Pest resistance.*—Not tested.

Wood:

*New wood.*—Color: Yellow-Green Group 144A. Bark: Smooth.

*Old wood.*—Color: Green Group 137C. Bark: Smooth.

Prickles:

*Quantity.*—On main canes from base: Ordinary. On laterals from main canes: Ordinary.

*Form.*—Hooked downward.

*Length.*—8–16 mm.

*Width.*—10–12 mm.

*Color when young.*—Greyed-Purple Group 184C.

*Color when mature.*—Greyed-Red Group 182B.

Small prickles:

*Quantity.*—On main stalks: None. On laterals: None.

Winter hardiness: Hardy to Zone 5.

I claim:

1. A new and distinct variety of rose plant of the hybrid tea class, substantially as herein shown and described, characterized particularly by light yellow flower color, good flower form, anise fragrance, long cut flower vase life, vigorous upright growth habit and large bloom size.

* * * * *

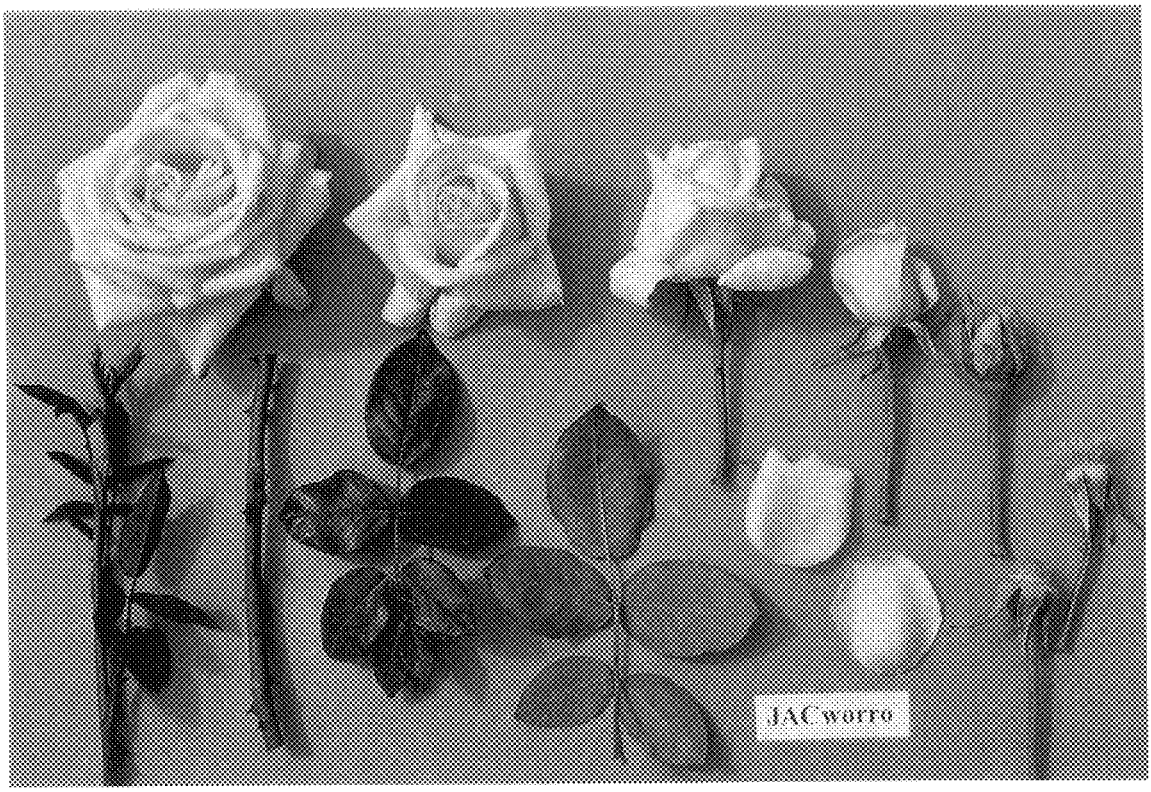
JAC worro